(12) United States Patent
Mahboobi et al.

(10) Patent No.: US 6,407,102 B1
(45) Date of Patent: Jun. 18, 2002

(54) INDOLE DERIVATIVES AND THEIR USE FOR THE TREATMENT OF MALIGNANT AND OTHER DISEASES BASED ON PATHOLOGICAL CELL PROLIFERATION

(75) Inventors: Siavosh Mahboobi, Regensburg; Sabine Kuhr, Westerstede; Herwig Pongratz, Regensburg; Alfred Popp, Burghausen; Harald Hufsky, Gaimersheim; Frank-D Bohmer, Dorndorf; Steffen Teller, Jena; Andrea Uecker, Neuengonna; Thomas Beckers, Frankfurt, all of (DE)

(73) Assignee: Zentaris AG, Frankfurt/Main (DE)

( * ) Notice: Subject to any disclaimer, the term of this patent is extended or adjusted under 35 U.S.C. 154(b) by 0 days.

(21) Appl. No.: 09/305,115

(22) Filed: May 4, 1999

(30) Foreign Application Priority Data

May 4, 1998 (DE) ........................................ 198 19 835
Aug. 25, 1998 (DE) ........................................ 198 38 506

(51) Int. Cl.$^7$ ........................ A61K 31/40; A61K 31/38; C07D 333/56; C07D 307/78
(52) U.S. Cl. ...................... 514/231.5; 548/499; 549/57; 549/468; 549/469; 514/443; 544/143
(58) Field of Search ................................ 514/419, 443, 514/465; 548/455; 549/57, 468, 469; 544/143

(56) References Cited

U.S. PATENT DOCUMENTS 3,598,583 A * 8/1971 Sprague

FOREIGN PATENT DOCUMENTS

| EP | 559 571 A1 | * 9/1993 |
| EP | 0778274 | 6/1997 |
| WO | 94/24117 | 10/1994 |
| WO | 95/17182 | 6/1995 |

OTHER PUBLICATIONS

A. Kondo et al., "Bisazo compound, its intermediate and their manufacture and electrophotographic photoreceptor with high–stability and durability", Chemical Abstracts, vol. 126, No. 10, 1997, pp. 711.

C. F. Nutaitis et al., "Reduction of heterocyclic alcohols with sodium borohydridr–trifluorocetic acid. preparation of bis–heterocyclic methanes", Chemical Abstracts, vol. 23, Nr. 4, 1991, pp. 403–411.

E. Fischer et al., "Synthesis of new sulfur heteroaromatics isoelectronic with dibenzo'g,p!chrysene by photocylization of thienyl–and phenyl–sunstituted ethenes", Journal of Organic Chemistry, vol. 61, Nr. 20, 1996, pp. 6997–7005.

O. Dann et al., "Trypanocide Diamidine mit vier Ringen in einem oder zwei Ringsystemen", Justus Liebigs Annalen Der Chemie, 1973, pp. 1112–1140.

M. Nagahara et al., "Synthesis and antiviral activity of bis(hydroxy–2–benzofuranyl) ketone derivative", Chemical Abstracts, vol. 105, Nr. 9, 1985, pp. 840–44.

M. Ahmed et al. "The direct Bradsher reaction. Part I. Synthesis of thiophen analogues of linear polycyclic hydrocarbons", Journal of the Chemical Society, Perkin Transactions 1, Nr. 10, 1973, pp. 1099–1103.

J.M. Gonzalez, "Process for the preparation of 2,2'–dibenzofurylic compounds", Chemical Abstracts, vol. 107, No. 5, 1987, pp. 678.

* cited by examiner

*Primary Examiner*—T. A. Solola
(74) *Attorney, Agent, or Firm*—Pillsbury Winthrop LLP

(57) ABSTRACT

The invention relates to tyrosine kinase inhibitors of the bis-indolyl compound type of the general formula I:

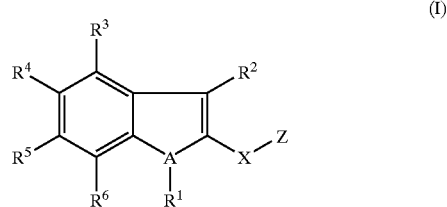

pharmaceuticals containing them and their use for the treatment of malignant and other diseases based on pathological cell proliferation.

11 Claims, No Drawings

INDOLE DERIVATIVES AND THEIR USE FOR THE TREATMENT OF MALIGNANT AND OTHER DISEASES BASED ON PATHOLOGICAL CELL PROLIFERATION

BACKGROUND OF THE INVENTION

1. Field of the Invention

The invention relates to tyrosine kinase inhibitors of the bis-indolyl compound type, pharmaceuticals containing them and their use for the treatment of malignant and other diseases based on pathological cell proliferation.

2. Background Information

The activation of tyrosine-specific protein kinases is a key event in stimulation of the division of animal cells. Normally, this stimulation is effected by exogenous factors, e.g. growth factors, when the proliferation of a certain cell type is necessary for the overall function of a tissue or organ. In tumours, cell proliferation is also linked with the activity of tyrosine kinases. In tumour cells, however, an aberrant activity of kinases is often present, which is caused by overexpression, constitutively active kinase mutants or ectopic activity of growth factors. The PDGF receptor is one of the growth factors with relevance for human tumours. PDGF is one of the main mitogens in the serum and is present in high concentrations in blood platelets. Its most important function in the adult body is wound healing. An undesired activity of the PDGF receptor is involved in the proliferation of various tumours, e.g. gliomas, glioblastomas, sarcomas, mastocarcinomas, ovarian carcinomas and colonic carcinomas. An aberrant activation of the PDGF/PDGF receptor system also assumes a key position in pathological hyperproliferation of mesenchymal cells in the context of arteriosclerosis, restenosis after balloon angioplasty, arthritis and fibrotic diseases.

A few growth factor receptor tyrosine kinases, whose tyrosine kinase domains have high sequence homology to the tyrosine kinase domain of the PGDF receptors, are also of importance for the tumour process and pathological hyperproliferation. These include the receptors for the vascular endothelial cell growth factor (VEGF)KDR/Flk-1 and Flt-1 with great importance for tumour vascularization, Kit/SCF receptor, for which constitutively active versions were observed in carcinomas and Flk-2/Flt-3, a receptor involved in the proliferation of leukemia cells of various forms of disease. It can be expected that further members of this kinase family with relevance for pathological proliferation will be identified. In addition to mitogenic stimulation, the actions of the ligands of these receptors often also include the stimulation of cell migration, anti-apoptotic actions and effects on membrane transport systems for ions, water and chemical compounds. To a varying extent, uncontrolled effects of this type are also involved in the pathological process in tumours and other diseases.

SUMMARY OF THE INVENTION

Of the various possibilities for switching off the signal of receptor tyrosine kinases, the specific direct inhibition of the activity of the kinase is the most promising.

The invention is therefore aimed at creating compounds which are suitable as inhibitors of tyrosine kinases, in particular of the PDGF receptor tyrosine kinases and further, related tyrosine kinases such as KDR/Flk-1, Kit/SCF receptor and FLK/Flt-3. This object is achieved by the compounds of the general formula I according to the invention:

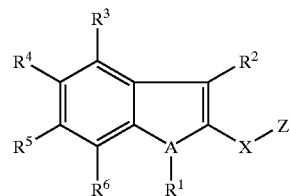
(I)

in which Z is a group having the general formula (II)

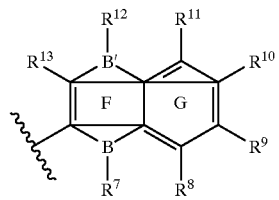
(II)

in which A can be nitrogen, oxygen or sulphur atoms and [sic] B, B' can be carbon, nitrogen, oxygen and sulphur atoms and the ring systems F and G independently of one another can be either saturated or unsaturated 5- and 6-membered rings, X is a group having the general formula III or IV

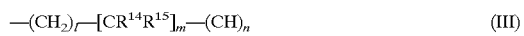
(III)

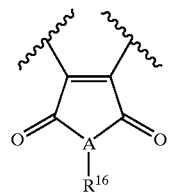
(IV)

in which A has the same meaning as above, 1 and n can assume the numbers from 0 to 6, m the numbers 1 and 2, and $R^{14}$ and $R^{15}$ either together form an oxygen atom or $R^{14}$ is a hydroxyl group and $R^{15}$ is a hydrogen atom or $R^{14}$ and $R^{15}$ are hydrogen atoms and where $R^{16}$ is a hydrogen atom, an alkyl or aryl radical, halogen-, amino-, or azido-substituted alkyl or aryl radical, an alkyloxymethyl or substituted alkyloxymethyl radical, $R^2$ and $R^{13}$ together form a linkage having the general formula V or VI

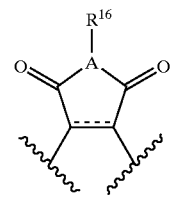
(V)

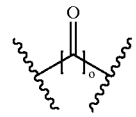
(VI)

where the dashed bond is a double or single bond, A and $R^{16}$ have the same meaning as above and o can assume the numbers 1 and 2, $R^2$ and $R^{13}$ are identical or different radicals of the general formula VII or hydrogen atoms,

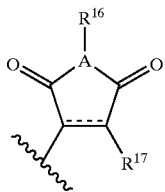

(VII)

where the dashed bond is a double or single bond, A and $R^{16}$ have the same meaning as above and $R^{17}$ is a halogen atom or a radical of the general formulae [sic] VIII

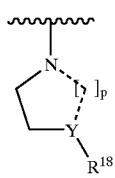

(VIII)

such that p can be=0, 1 or 2 (if p=0 then it is an acyclic primary amine and Y carries an additional hydrogen atom), Y can be a carbon, oxygen or nitrogen atom and if Y is a carbon or nitrogen atom, $R^{18}$ is a hydrogen atom or an alkyl or aryl radical, substituted alkyl or aryl radical, saturated or unsaturated heterocycle, alkoxycarbonyl radical, aminocarbonylmethyl radical or substituted aminocarbonylmethyl radical, $R^2$ and $R^{13}$ together form a linkage having the general formula IX or X

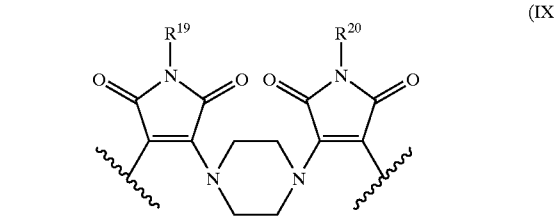

(IX)

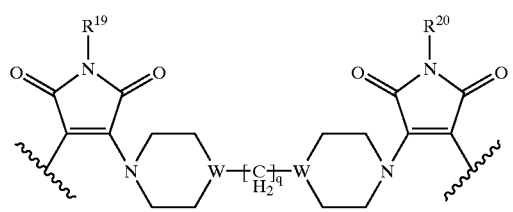

(X)

where W is either a carbon or a nitrogen atom, q can assume a value between 0 and 6 and $R^{19}$ and $R^{20}$ can be hydrogen atoms, alkyl radicals or substituted alkyl radicals, in which $R^1$ and $R^7$ are identical or different and are hydrogen atoms, alkyl or aminoalkyl radicals, phenylsulphonyl radicals, alkylsilylmethoxymethyl radicals, a sugar or substituted sugar, where $R^3$, $R^4$, $R^5$, $R^6$, $R^8$, $R^9$, $R^{10}$ and $R^{11}$ are identical or different and in each case is a hydrogen atom, an alkoxy-, amino-, halogen-, cycloalkyl-, cycloheteroalkyl-, aryl- or heteroaryl-substituted alkyl, alkoxy or alkoxymethyl group, nitro group, a halogen atom or an O-alkoxy group of the general form —O—(C=O)—$R^{21}$, where $R^{21}$ are [sic] an alkoxy-, amino-, halogen-, cycloalkyl-, cycloheteroalkyl-, aryl- or heteroaryl-substituted alkyl, alkoxy or alkoxymethyl group.

Preferred compounds according to the invention are those having the above general formulae [sic] I, in which Z is a group having the general formula II and X is a group having the general formula III, $R^2$ and $R^{13}$ are hydrogen atoms, A is a nitrogen atom and B is a nitrogen, oxygen or sulphur atom and $R^3$, $R^4$, $R^5$, $R^6$, $R^7$, $R^8$, $R^9$, $R^{10}$, $R^{11}$, $R^{14}$ and $R^{15}$ have the same meaning as above, where these compounds correspond to the following formula XI:

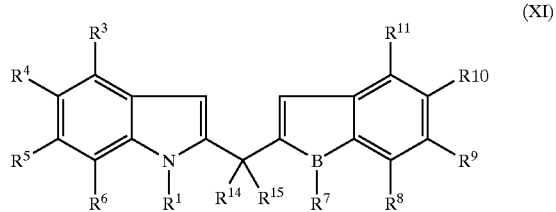

(XI)

Particularly preferred compounds are those of the formula XI in which $R^{14}$ and $R^{15}$ together form an oxygen atom.

Additionally preferred compounds according to the invention are those having the above general formula I in which Z is a group having the general formula II and X is a group having the general formula III, $R^1$ and $R^2$ are hydrogen atoms, A and B are nitrogen atoms, and $R^1$, $R^3$, $R^4$, $R^5$, $R^6$, $R^7$, $R^{8,}$ $R^9$, $R^{10}$, $R^{11}$ and $R^{16}$ have the same meaning as above, where these compounds correspond to the following formula XII:

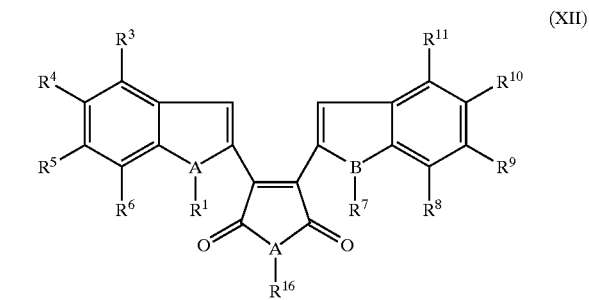

(XII)

Additionally preferred compounds according to the invention are those having the general formulae XIII and XIV below

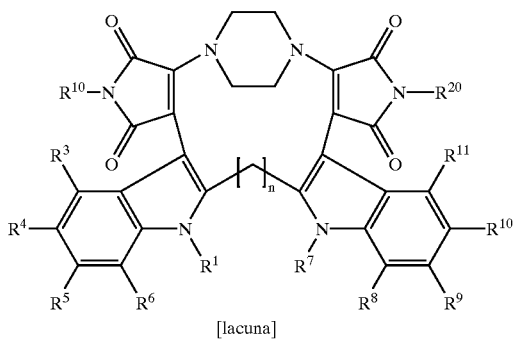

[lacuna]

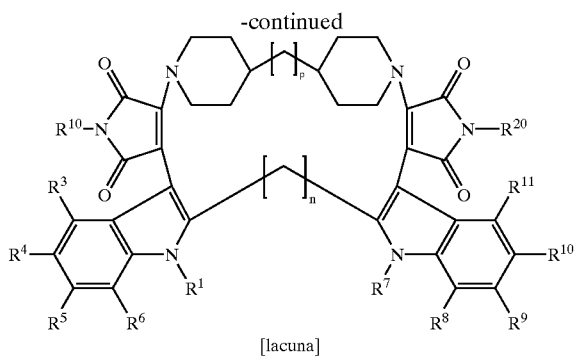

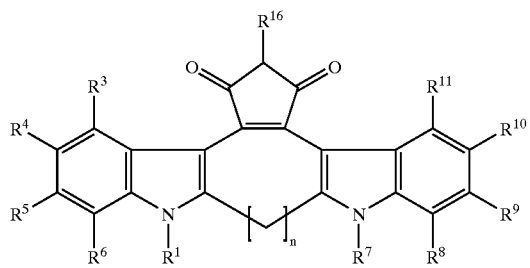

in which n is the numbers 3, 4, 5, 8 or 12, q is the numbers 0, 1, 2, 3, 5 or 6, $R^{19}$, $R^{20}$ are hydrogen atoms or alkyl groups and $R^1$, $R^3$, $R^4$, $R^5$, $R^6$, $R^7$, $R^8$, $R^9$, $R^{10}$, $R^{11}$ and $R^{16}$ are identical or different and have the same meaning as above.

Additionally preferred compounds according to the invention are those having the following general formula XV in which n is the numbers 1, 2 or 3, $R^{16}$ is a hydrogen atom or an alkyl group and $R^1$, $R^3$, $R^4$, $R^5$, $R^6$, $R^7$, $R^8$, $R^9$, $R^{10}$, $R^{11}$ and $R^{16}$ are identical or different and have the same meaning as above.

The compounds of the formula XI can be prepared by one of the two following schemes:

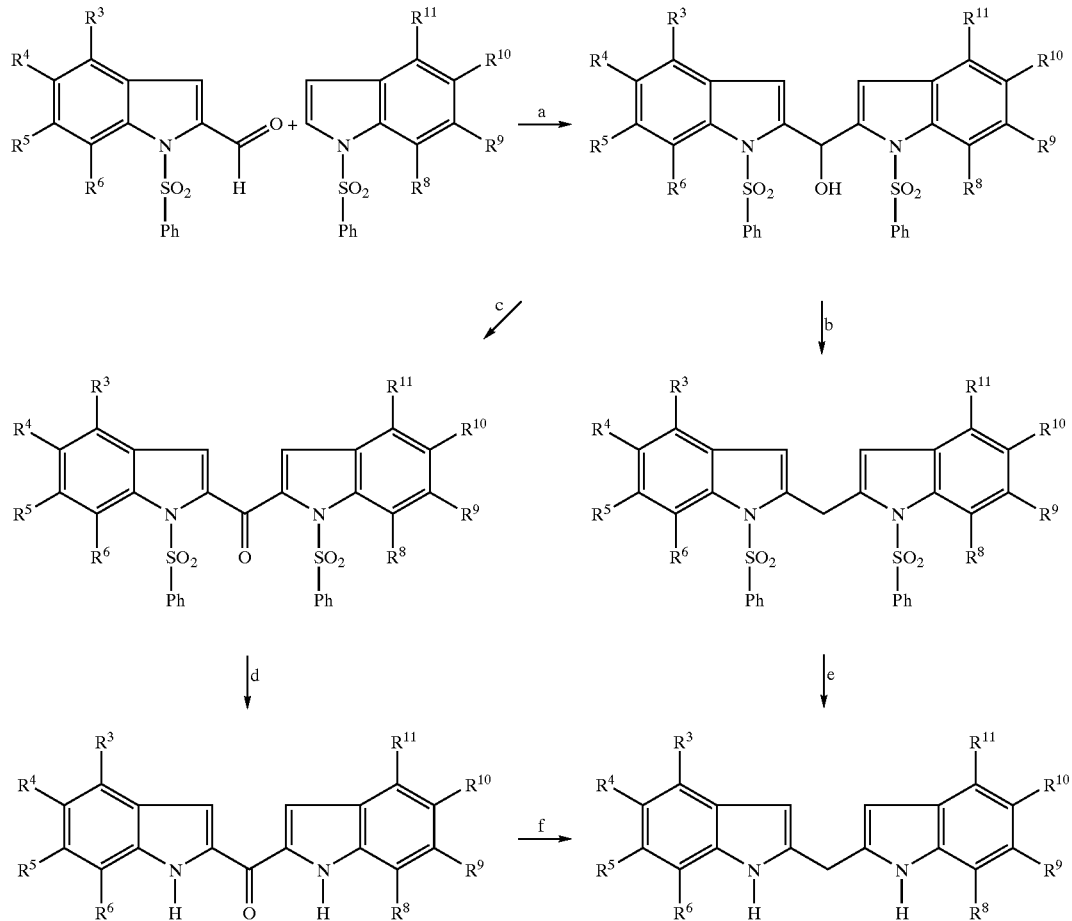

a) LDA/THF, b) HSiPh$_3$/THF, c) PDC/DMF, d) 10% NaOH/Et6OH, e) K$_2$CO$_3$/MeOH,
f) N$_2$H$_4$/2-(2-hydroxyethyloxy)-ethanol

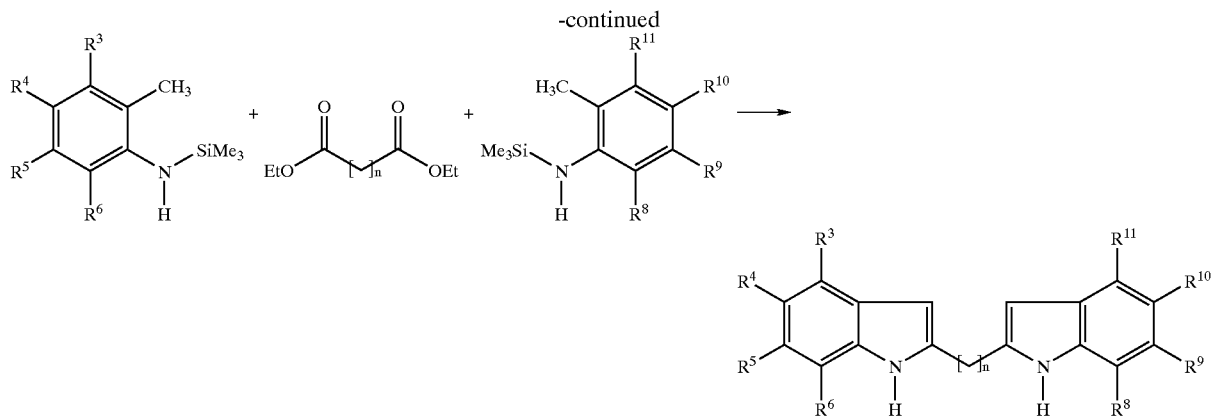

n = 2 or 3

For the preparation of the compounds according to the invention in which $R^2$ and $R^{13}$ are a radical of one of [sic] the above general formula VII or together form a linkage having the general formula V, IX or X, a 2,2'-bis-1H-indolylalkane or a derivative thereof having the general formula XI

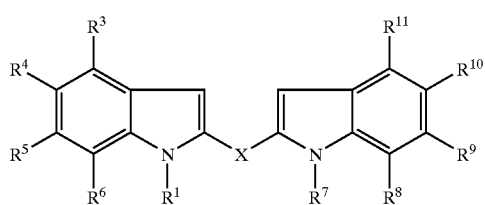

(XI)

in which X, $R^1$, $R^3$, $R^4$, $R^5$, $R^6$, $R^7$, $R^8$, $R^9$, $R^{10}$ and $R^{11}$ have the same meaning as above, is initially reacted with dibromomaleimide.

Compounds according to the invention in which $R^2$ and $R^{13}$ together form a linkage having the general formula VII are then reacted with a primary or secondary amine of the following general structures [sic] XVI, XVII or piperazine

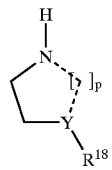

(XVI)

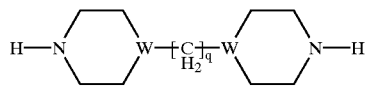

(XVII)

in which p, q, $R^{17}$ and W have the same meaning as above.

DETAILED DESCRIPTION OF THE INVENTION

The following examples illustrate the invention, without restricting it.

EXAMPLE 1
Bis(N-phenylsulphonylindol-2-yl)-1-methanol

Lithium diisopropylamide is prepared at −78° C. from 30.40 ml (216.3 mmol) of diisopropylamine and 125.3 ml (200.5 mmol) of n-BuLi (1.6 M in hexane) in 200 ml of absol. THF. The solution is stirred at −78° C. for 10 min and then at 0° C. for 30 min, before 49.13 g (190.9 mmol) of 1-phenylsulphonylindole in 300 ml of absol. THF are added dropwise at 0° C. in the course of 10 min. The reaction solution is stirred at 0° C. for a further 30 min. After cooling again to −78° C., 60.00 g (210.3 mmol) of phenylsulphonyl-2-carbaldehyde in 200 ml of absol. THF are added dropwise and the mixture is allowed to warm to room temp. overnight. The mixture is poured onto 1 percent HCl and the org. phase is separated off after addition of of [sic] ether. The aq. phase is extracted with ether, and the combined org. phases are washed successively with $NaHCO_3$ and satd. NaCl solution and dried over $Na_2SO_4$. The solvent is Stripped [sic] off in vacuo and the crude product is purified by column chromatography ($SiO_2$; $CH_2Cl_2$): colourless crystals, yield 86.5 g (84%).

M.p.: 185° C. (MeOH).

The following were prepared analogously:

EXAMPLE 2
Bis(5-methoxy-N-phenylsulphonylindol-2-yl)-1-methanol
M.p.: 113–114° C. (MeOH)

EXAMPLE 3
(5-Methoxy-N-phenylsulphonylindol-2-yl)-(N-phenylsulphonylindol-2-yl)-1-methanol
M.p.: 104–105° C. ($CH_2Cl_2$/hexane)

EXAMPLE 4
(5-Methoxy-N-phenylsulphonylindol-2-yl)-(7-methoxy-N-phenylsulphonylindol-2-yl)-1-methanol
M.p.: 119–121° C. ($CH_2Cl_2$/hexane)

EXAMPLE 5
(5-Methoxy-N-phenylsulphonylindol-2-yl)-(N-phenylsulphonylindol-2-yl)-1-methanol
M.p.: 99–101° C. ($CH_2Cl_2$/hexane)

EXAMPLE 6
(5-Methoxy-2-phenylmethyloxy(1-phenylsulphonylindol-2-yl)methyl-1-phenylsulphonylindol
M.p.: 62–64° C.

EXAMPLE 7
Di-(5-Methyloxy-1-phenylsulphonylindol-2-yl)
phenylmethyloxymethane
M.p.: 100–101° C.

EXAMPLE 8
(3-Dimethylaminomethyl-1-phenylsulphonylindol-2-yl)(1-
phenylsulphonylindol-2-yl)methan-1-ol
M.p.: 116–117° C.

EXAMPLE 9
(7-Methoxy-N-phenylsulphonylindol-2-yl)(N-
phenylsulphonylindol-2-yl)-1-methanol
M.p.: 149–151° C.

EXAMPLE 10
Dibenzothiophen-2-yl-1-methanol
M.p.: 130–131° C.

EXAMPLE 11
6-Methoxy-1-phenylsulphonyl-1H-2-indolyl(1-
phenylsulphonyl-1H-2-indolyl)methanol
M.p.: 180° C.

EXAMPLE 12
7-Methoxy-1-phenylsulphonyl-1H-2-indolyl(1-
phenylsulphonyl-1H-2-indolyl)methanol
M.p.: 148–150° C.

EXAMPLE 13
Benzo[b]thiophen-2-yl(5-methoxy-1-phenylsulphonyl-1H-
2-indolyl)-1-methanol
M.p.: 71–73° C.

EXAMPLE 14
Benzo[b]thiophen-2-yl(7-methoxy-1-phenylsulphonyl-1H-
2-indolyl)-1-methanol
M.p.: 118–119° C.

EXAMPLE 15
Benzo[b]furan-2-yl(5-methoxy-1-phenylsulphonyl-1H-2-
indolyl)-1-methanol
M.p.: 71–73° C.

EXAMPLE 16
Bis (N-phenylsulphonylindol-2-yl)methan-1-one

The solution of 20.00 g (36.9 mmol) of bis-(N-phenylsulphonylindol-2-yl)-1-methanol in 200 ml of absol. DMF is cooled to 0° C. After addition of 90.4 g of pyridinium dichromate (PDC), it is stirred at room temp. for 20 h. For work-up, 700 ml of $H_2O$ and 700 ml of $CH_2Cl_2$ are added. The aq. phase is extracted with 2×200 ml of $CH_2Cl_2$. The combined org. extracts are washed with 500 ml of $H_2O$. After stripping of the solvent in vacuo and addition of $CH_2Cl_2$, the product precipitates: colourless crystals, yield 15.0 g (75%).
M.p.: 244° C. (MeOH/ether)

The following were prepared analogously:

EXAMPLE 17
(5-Methoxy-N-phenylsulphonylindol-2-yl)-(N-
phenylsulphonylindol-2-yl)methan-1-one
M.p.: 205° C. (MeOH)

EXAMPLE 18
Bis(5-methoxy-N-phenylsulphonylindol-2-yl)-1-methanone

EXAMPLE 19
Bisindol-2-ylmethan-1-one 10.0 g (18.5 mmol) of bis(N-phenylsulphonylindol-2-yl) methan-1-one are dissolved in 380 ml of 99 percent EtOH. After addition of 210 ml of 10 percent NaOH, the solution is heated under reflux for 20 H. For work-up, the EtOH is stripped off, 500 ml of satd. NaCl solution and 500 ml of $CH_2Cl_2$ are added and the phases are separated. The aq. phase is extracted with 2×200 ml of $CH_2Cl_2$, and the combined org. extracts are dried over $Na_2SO_4$ and concentrated in vacuo. The bisindole is deposited as a crude product and can be recrystallized from $CH_2Cl_2$, yellow crystals, yield 4.5 g (93%)
M.p.: 272–273° C. ($CH_2Cl_2$)

The following were prepared analogously:

EXAMPLE 20
(5-Methoxyindol-2-yl)-(indol-2-yl)methan-1-one
M.p.: 233–235° C. (MeOH)

EXAMPLE 21
Bis(5-methoxyindol-2-yl)-1-methanone
M.p.: 202–204° C.

EXAMPLE 22
Dibenzothiophen-2-yl-1-methanone
M.p.: 161° C.

EXAMPLE 23
5-Methyl-1-phenylsulphonyl-3-indolyl(1-phenylsulphonyl-
2-indolyl)-1-methanone
M.p.: 114–116° C.

EXAMPLE 24
(1H-Indol-2-yl)-(1H-indol-3-yl)-1-methanone
M.p.: 260–261° C. (MeOH)

EXAMPLE 25
Benzo[b]thiophen-2-yl(7-methoxy-1-phenylsulphonyl-1H-
2-indolyl)-1-methanone
M.p.: 190° C.

EXAMPLE 26
Benzo[b]thiophen-2-yl(7-methoxy-1H-2-indolyl)-1-
methanone
M.p.: 155° C.

EXAMPLE 27
Benzo[b]thiophen-2-yl(5-methoxy-1-phenylsulphonyl-1H-
2-indolyl)-1-methanone
M.p.: 82–83° C.

EXAMPLE 28
Benzo[b]thiophen-2-yl(5-methoxy-1H-2-indolyl)-1-
methanone
M.p.: 200° C.

EXAMPLE 29
7-Methoxy-1-phenylsulphonyl-1H-2-indolyl(1-
phenylsulphonyl-1H-2-indolyl)methanone
M.p.: 129–130° C.

EXAMPLE 30
7-Methoxy-1H-2-indolyl(1H-2-indolyl)methanone
M.p.: 151° C.

EXAMPLE 31
6-Methoxy-1-phenylsulphonyl-1H-2-indolyl(1-
phenylsulphonyl-1H-2-indolyl)methanone
M.p.: 184–186° C.

EXAMPLE 32
6-Methoxy-1H-2-indolyl(1H-2-indolyl)methanone
M.p.: 184–186° C.

EXAMPLE 33
1-Methyl-1H-2-indolyl(1-ethyl-5-methyloxy-1H-2-indolyl)-1-methanone
M.p.: 148–149° C.

EXAMPLE 34
1H-2-Indolyl(1-methyl-5-methyloxy-1H-2-indolyl)-1-methanone
M.p.: 190° C.

EXAMPLE 35
1-Methyl-1H-2-indolyl(5-methyloxy-1H-2-indolyl)-1-methanone
M.p.: 176–177° C.

EXAMPLE 36
1-Ethyl-1H-2-indolyl(1-ethyl-5-methyloxy-1H-2-indolyl)-1-methanone
M.p.: 99–100° C.

EXAMPLE 37
1H-2-Indolyl(1-ethyl-5-methyloxy-1H-2-indolyl)-1-methanone
M.p.: 142–143° C.

EXAMPLE 38
1-Ethyl-1H-2-indolyl(5-methyloxy-1H-2-indolyl)-1-methanone
M.p.: 101–102° C.

EXAMPLE 39
1-Benzyl-1H-2-indolyl(1-benzyl-5-methoxy-1H-2-indolyl)-1-methanone
M.p.: 132° C.

EXAMPLE 40
1H-2-indolyl(1-benzyl-5-methoxy-1H-2-indolyl)-1-methanone
M.p.: 180–182° C.

EXAMPLE 41
1-Benzyl-1H-2-indolyl(5-methoxy-1H-2-indolyl)-1-methanone
M.p.: 167–168° C.

EXAMPLE 42
5-Benzyloxy-1H-2-indolyl(1H-2-indolyl)methanone
M.p.: 199–201° C.

EXAMPLE 43
5-Hydroxy-1H-2-indolyl(1H-2-indolyl)methanone
M.p.: >220° C.

EXAMPLE 44
5-Ethoxy-1H-2-indolyl(1H-2-indolyl)methanone
M.p.: 168–169° C.

EXAMPLE 45
1H-2-Indolyl[5-(2-morpholin-1-yle-hyloxy)-1H-2-indolyl]methanone
M.p.: 98–101° C.

EXAMPLE 46
1H-2-Indolyl[5-(3-dimethylaminopropyloxy)-1H-2-indolyl]methanone
M.p.: 163–166° C.

EXAMPLE 47
5-(4-Iodobutyloxy)-1H-2-indolyl(1H-2-indolyl)methanone
M.p.: 110–113° C.

EXAMPLE 48
1H-2-Indolyl[5-(2-dimethylaminoethyloxy)-1H-2-indolyl]methanone
M.p.: 143–145° C.

EXAMPLE 49
5-Cyclohexylmethyloxy-1H-2-indolyl(1H-2-indolyl)-methanone
M.p.: 185° C. (dec.)

EXAMPLE 50
5-(5-Iodopentyloxy)-1H-2-indolyl(1H-2-indolyl)methanone
M.p.: 127–130° C.

EXAMPLE 51
1H-2-Indolyl[5-(1-phenylethyloxy)-1H-2-indolyl]-methanone
M.p.: 151–153° C.

EXAMPLE 52
1H-2-Indolyl[5-(2-piperidin-1-ylethyloxy)-1H-2-indolyl]methanone
M.p.: 104–106° C.

EXAMPLE 53
[2-(1H-2-Indolylcarbonyl)-1H-5-indolyl)] [sic] ethanoate
M.p.: 223–224° C.

EXAMPLE 54
[2-(1H-2-Indolylcarbonyl)-1H-5-indolyl)] [sic] 4-methoxybenzoate
M.p.: >230° C.

EXAMPLE 55
[2-(1H-2-Indolylcarbonyl)-1H-5-indolyl)] [sic] butanoate
M.p.: 201–204° C.

EXAMPLE 56
[2-(1H-2-Indolylcarbonyl)-1H-5-indolyl)] [sic] 2-(N,N)-dimethylaminoethanoate
M.p.: 215–217° C.

EXAMPLE 57
[2-(1H-2-Indolylcarbonyl)-1H-5-indolyl)] [sic] propanoate
M.p.: >230° C.

EXAMPLE 58
[2-(1H-2-Indolylcarbonyl)-1H-5-indolyl)] [sic] 2-thiophenylethanoate
M.p.: 224–226° C.

EXAMPLE 59
[2-(1H-2-Indolylcarbonyl)-1H-5-indolyl)] [sic] O-acetyl-salycylate [sic]
M.p.: 133–135° C.

EXAMPLE 60
[2-(1H-2-Indolylcarbonyl)-1H-5-indolyl)] [sic] 4-phenylbenzoate
M.p.: >220° C.

EXAMPLE 61
[2-(1H-2-Indolylcarbonyl)-1H-5-indolyl)] [sic] 2-phenylpropanoate
M.p.: 211–313° C. [sic]

EXAMPLE 62
[2-(1H-2-Indolylcarbonyl)-1H-5-indolyl)] [sic] α-acetyl-phenylethanoate
M.p.: 194–196° C.

EXAMPLE 63
[2-(1H-2-Indolylcarbonyl)-1H-5-indolyl)] [sic] benzoate
M.p.: >230° C.

EXAMPLE 64
[2-(1H-2-Indolylcarbonyl)-1H-5-indolyl)] [sic] 3-methoxyphenylethanoate
M.p.: 212–215° C.

EXAMPLE 65
[2-(1H-2-Indolylcarbonyl)-1H-5-indolyl)] [sic] 2-chlorobenzoate
M.p.: >230° C.

EXAMPLE 66
[2-(1H-2-Indolylcarbonyl)-1H-5-indolyl)] [sic] 4-nitrobenzoate
M.p.: >230° C.

EXAMPLE 67
[2-(1H-2-Indolylcarbonyl)-1H-5-indolyl)] [sic] 3,4,5-trimethoxybenzoate
M.p.: 216–219° C.

EXAMPLE 68
[2-(1H-2-Indolylcarbonyl)-1H-5-indolyl)] [sic] cinnamate
M.p.: 226–228° C.

EXAMPLE 69
[2-(1H-2-Indolylcarbonyl)-1H-5-indolyl)] [sic] 2-furanylcarboxylate [sic]
M.p.: >230° C.

EXAMPLE 70
Di(1-phenylsulphonyl-1H-2-indolyl)methane 22.4 ml of trifluoroacetic acid (TFA) are added dropwise after 30 min to a solution of 26.67 g (49.2 mmol) of bis(N-phenylsulphonylindol-2-yl)-1-methanol and 15.00 g (57.8 mmol) of triphenylsilane in 400 ml of absol. $CH_2Cl_2$. After stirring at room temp. for 1 h, $H_2O$ is added and the mixture is cautiously neutralized with solid $Na_2CO_3$ with ice-cooling. After separating the phases, drying the org. phase over $Na_2SO_4$ and distilling off the solvent, the crude product is purified by column chromatography ($SiO_2$; $CH_2Cl_2$/hexane 6:4), colourless crystals, yield 22.5 g (87%).
M.p.: 144–145° C. (ether)
The following were prepared analogously:

EXAMPLE 71
Bis(5-methoxy-N-phenylsulphonylindol-2-yl)methane
M.p.: 159–160° C. ($CH_2Cl_2$/hexane)

EXAMPLE 72
(5-Methoxy-N-phenylsulphonylindol-2-yl)-(N-phenylsulphonylindol-2-yl)methane
M.p.: 98–100° C. ($CH_2Cl_2$/hexane)

EXAMPLE 73
(5-Methoxy-N-phenylsulphonylindol-2-yl)-(7-methoxy-N-phenylsulphonylindol-2-yl)methane
M.p.: 168–170° C. ($CH_2Cl_2$/hexane)

EXAMPLE 74
Di(1H-2-indolyl)methane 15.0 g (28.5 mmol) of 57 are boiled with 20 g of $K_2CO_3$ in 800 ml of MeOH and 200 ml of $H_2O$ for 14 days. For work-up, 500 ml of satd. NaCl solution are added and the phases are separated. After drying the org. phase, the solvent is stripped off in vacuo. The crude product is purified by column chromatography, colourless crystals, yield 5.4 g (76%).

M.p.: 189–191° C.
The following were prepared analogously:

EXAMPLE 75
(5-Methoxyindol-2-yl)-(indol-2-yl)methanone
M.p.: 112° C. (MeOH)

EXAMPLE 76
(1H-Indol-2-yl)-(1-H-indol-3-yl)-1-methane
M.p.: 161–163° C. (aq. EtOH)

EXAMPLE 77
1,3-Di(1H-2-indolyl)propane 38.0 g (0.21 mol) of trimethylsilyl-o-toluidide are dissolved in 950 ml of abs. hexane and 291.0 ml (0.47 mol) of n-BuLi (1.6 M in hexane) are added dropwise at room temp. and the mixture is heated to reflux for 4 h. It is then cooled to −78° C. and 20.5 ml (0.11 mol) of diethyl glutarate in 380 ml of abs. THF are added dropwise at this temp. The mixture is stirred at −78° C. for 1 h, and is then slowly allowed to come to room temp. overnight and subsequently heated to boiling for a further 2 h. After cooling, it is poured onto 1 l of ice water and extracted with 5×500 ml of ethyl acetate, the combined org. phases are dried over $Na_2SO_4$ and the solvent is stripped off in vacuo. White crystals, yield 6.55 g (23.9 mmol, 22%).
M.p.: 143–145° C. (ethanol)
The following was prepared analogously:

EXAMPLE 78
1,3-Di(1H-2-indolyl)ethane
M.p.: 264–267° C.

EXAMPLE 79
1,2-Di-(1-phenylsulphonyl-1H-2-indolyl)-1-ethene

[lacuna] (17.9 mmol) of $TiCl_4$ with a syringe and 2.0 g (30.5 mmol) of Zn powder are subsequently added. The mixture is heated under reflux for 30 min. After this, 3 g (10.5 mmol) of 22, dissolved in 50 ml of THF, are added dropwise again at 0° C. The solution is heated under reflux overnight. 300 ml of 20 percent $K_2CO_3$ soln. are poured into the cooled solution and it is stirred further overnight at room temp. The sludgy residue is then filtered off and washed with THF, the org. phase is separated off from the filtrate and the aqueous phase is extracted with $CH_2Cl_2$. The combined org. phases are washed with water, dried over $Na_2SO_4$ and freed from the solvent in vacuo. Purification is carried out by column chromatography ($SiO_2$; $CH_2Cl_2$/hexane 2:1). Yield: 1.1 g (2.0 mmol, 39%) of yellow crystals.
M.p.: 272° C.

EXAMPLE 80
Bis(5-methoxy-N-phenylsulphonylindol-2-yl)phenoxymethane 188 mg of NaH (60% in paraffin) are added at 0° C. to a solution of 2 g (3.7 mmol) of bis(-N-phenylsulphonylindol-2-yl)-1-methanol in 20 ml of THF. 13.5 mg of tetrabutylammonium iodide and 0.45 ml of benzyl bromide are subsequently added and the mixture is stirred at 20° C. Water and ether are then cautiously added, the ether phase is separated off and the aqueous phase is washed twice with ether. The org. phase is dried over $Na_2SO_4$ and the solvent is then stripped off. Yield: 0.86 mg (81%)
M.p.: 192° C. (dec.)

EXAMPLE 81
1,2,3,8,9,10-Hexahydroindolo[3',2':5,6]pyrrolo-[3',4':3,4]-cyclohepta[b]indole-1,3-dione Half of 0.73 ml (9.75 mmol) of anhydrous ethyl bromide is added to 236 mg (9.75 mmol) of Mg turnings in 6 ml of absol. THF. After the reaction has started, the remainder of the ethyl bromide is added dropwise such that the solution continues to boil. It is then boiled until the Mg turnings have dissolved (about 30 min). After cooling to room temp., 1.00 g (4.06 mmol) of methylene-2,2'-bisindole in 25 ml of absol. toluene and 1 ml of absol. THF is added dropwise and the mixture is stirred at 45° C. for 45 min [sic]. After cooling to room temp. again, 1.04 g (4.06 mmol) of dibromomaleimide in 50 ml of absol. toluene and 2 ml of absol. THF are added dropwise over the course of 1 h, then the mixture is heated under reflux overnight. For work-up, 100 g of ice and 50 ml of 20 percent citric acid are added, then the mixture is extracted by shaking with 2×50 ml of ethyl acetate. The org. extracts are washed with $H_2O$, dried over $Na_2SO_4$ and concentrated. The crude product is purified by column chromatography ($SiO_2$, 1. $CH_2Cl_2$/ethyl acetate 8:2; 2. $CH_2Cl_2$/ethyl acetate 7:1): red crystals, yield 290 mg (22%) m.p.: >350° C. (ethyl acetate).

The following were prepared analogously:

EXAMPLE 82
1,2,3,8,9,10-Hexahydro-5-methoxyindolo[3',2':5,6]-pyrrolo[3',4':3,4]-cyclohepta[b]indole-1,3-dione M.p.: >350° C. (EtOH)

EXAMPLE 83
1,2,3,8,9,10,11,12-Octahydroindolo[3',2':5,6]pyrrolo-[3',4':3,4]cyclonona[b]indole-1,3-dione M.p.: 137° C. ($CH_2Cl_2$) (dec.)

EXAMPLE 84
1,2,3,8,9,10,11-Heptahydro-2-methylindolo[3',2':5,6]-pyrrolo[3',4':3,4]-cycloocta[b]indole-1,3-dione M.p.: >350° C.

EXAMPLE 85
2-Benzyloxymethyl-1,2,3,8,9,10-hexahydroindolo-[3',2':5,6]-pyrrolo[3',4':3,4]-cyclohepta[b]indole-1,3-dione M.p.: >350° C. (EtOH)

EXAMPLE 86
1,2,3,8,9,10,-Hexahydro-2-methylindolo[3',2':5,6]-pyrrolo[3',4':3,4]-cyclohepta[b]indole-1,3,dione M.p.: >350° C. ($CH_2Cl_2$)

EXAMPLE 87
3,8,9,10-Tetrahydro-8-[2-(N,N-dimethylamino)ethyl]-1H-indolo[3',2':5,6]furo[3',4':3,4]cyclohepta[b]indole-1,3-dione M.p.: >350° C. (MeOH)

EXAMPLE 88
2-Benzyloxymethyl-1,2,3,8,9,10-hexahydro-8-[2-(N,N-dimethylamino)ethyl]indolo[3',2':5,6]pyrrolo[3',4':3,4]-cyclohepta[b]indole-1,3-dione M.p.: 164–165° C. (MeOH)

EXAMPLE 89
1,2,3,8,9,10-Hexahydro-3-methyl-8-[2-(N,N-dimethylamino)ethyl]indolo[3',2':5,6]pyrrolo[3',4':3,4]-cyclohepta[b]indole-1,3-dione M.p.: 185° C. (MeOH)

EXAMPLE 90
1,2,3,8,9,10-Hexahydro-8-[2-(N,N-dimethylamino)ethyl]-indolo[3',2':5,6]pyrrolo[3',4':3,4]cyclohepta[b]indole-1,3-dione M.p.: 213–214° C. (EtOH)

EXAMPLE 91
3-Bromo-4-(2-(2-(1H-2-indolyl)ethyl)-1H-3-indolyl)-1-methyl-2,5-dihydro-1H-pyrrole-2,5-dione M.p.: 169° C.

EXAMPLE 92
3-Bromo-4-(2-(4-(1H-2-indolyl)butyl)-1H-3-indolyl)-1-methyl-2,5-dihydro-1H-pyrrole-2,5-dione M.p.: 165° C. (dec.)

EXAMPLE 93
3-Bromo-4-(2-(5-(1H-2-indolyl)pentyl)-1H-3-indolyl)-1-methyl-2,5-dihydro-1H-pyrrole-2,5-dione M.p.: 125° C. (dec.)

EXAMPLE 94
Bis(indol-3-yl)methanone

Analogously to Example 31 using triphosgene instead of dibromomaleimide.

M.p.: 297–299° C.

EXAMPLE 95

Diastereomer mixture of 8-(3,4,6-tri-O-benzyl-b[sic]-D-glucopyransoyl)-2-benzyloxymethyl-1,2,3,8,9,10-hexahydroindolo[3',2':5,6]pyrrolo[3',4':3,4]cyclohepta[b]-indole-1,3-dione and 8-(3,4,6-tri-O-benzyl-a[sic]-D-mannopyranosyl)-2-benzyloxymethyl-1,2,3,8,9,10-hexahydroindolo-[3',2':5,6]pyrrolo[3',4':3,4]cyclohepta[b]indole-1,3-dione Diastereomer mixture of the disubstituted O-glycosides 468.7 mg (1.02 mmol) of 2-benzyloxymethyl-1,2,3,8,9,10-hexahydroindolo[3',2':5,6]pyrrolo[3',4':3,4]cyclohepta-[b]indole-1,3-dione are added to a suspension of 91.8 mg (3.06 mmol) of NaH (80% in paraffin oil) in 16 ml of absol. THF. After 30 min, the solution of 1,2-anhydro-3,4,6-tri-O-benzyl-D-glucopyranose in 16 ml of absol. THF is added dropwise. The mixture is stirred at 50° C. for 5 h and at 60° C. for 1 h. For work-up, the reaction solution is poured onto 10 ml of satd. $NaHCO_3$ solution and extracted with 3×10 ml of ethyl acetate. The combined org. extracts are washed with 15 ml of satd. NaCl solution, dried over $Na_2SO_4$ and concentrated in vacuo. The product is separated by column chromatography (1. column: $SiO_2$; toluene/isopropylamine 8:2; 2. column: $SiO_2$; $CH_2Cl_2$/MeOH 12:1) from by-products and unreacted starting material. The diastereomer mixture is separated by HPLC.

EXAMPLE 96
Diastereomer mixture of 8-(b[sic]-D-glucopyranosyl)-1,2,3,8,9,10-hexahydroindolo[3',2':5,6]pyrrolo-[3',4':3,4]cyclohepta[b]indole-1,3-dione and 8-(a[sic]-D-mannopyranosyl)-1,2,3,8,9,10-hexahydroindolo-[3',2':5,6]pyrrolo[3',4':3,4]cyclohepta[b]indole-1,3-dione 150 mg (0.17 mmol) 8-(3,4,6-tri-O-benzyl-2-benzyloxymethyl-D-glucopyranosyl)-1,2,3,8,9,10-hexahydroindolo[3',2':5,6]pyrrolo[3',4':3,4]cyclohepta[b]indole-1,3-dione, as a diastereomer mixture, are dissolved in 50 ml of absol. EtOH and, after the addition of 200 mg of Pd/C (5%), the solution is stirred under an $H_2$ pressure of 7 bar for 5 h. It is then filtered off with suction through Celite, rinsed with 50 ml of $CH_2Cl_2$ and the solution is concentrated in vacuo. Without purification, the product is dissolved in 15 ml of absol. THF and the solution is cooled to 0° C. $NH_3$ is then passed in for 10 min and the mixture is stirred at room temp. for 1 h. After stripping off the THF in vacuo, the residual oil is purified by column chromatography (SiO$_2$: CH$_2$Cl$_2$/MeOH 8:2): red oil, yield 10 mg (12%).

EXAMPLE 97
1,2,3,3a,8,9,10,14c-Octahydroindolo[3',2':5,6]pyrrolo-[3',4':3,4]cyclohepta[b]indole-1,3-dione 1.20 g (18.4 mmol) of Zn granules are washed with 2×3 ml of 2 N HCl, then immediately added to 90 mg (0.33 mmol) of HgCl$_2$ in 1.5 ml of H$_2$O and 1.5 ml of conc. HCl and the mixture is shaken at room temp. for 10 min. The aq. phase is decanted and the zinc amalgam is additionally washed with 2×3 ml of dil. HCl before it is added to a solution of 60.0 mg (0.18 mmol) of 1,2,3,8,9,10-hexahydroindolo[3',2':5,6]pyrrolo-[3',4':3,4]cyclohepta[b]indole-1,3-dione in 1.5 ml of 5 N HCl, 1.5 ml of EtOH and 1.5 ml of toluene and heated under reflux. After 1 h, as soon as the reaction solution has cooled to room temp. H$_2$O is added and the mixture is extracted with 2×10 ml of CH$_2$Cl$_2$. The org. extracts are dried over Na$_2$SO$_4$, concentrated in vacuo and purified by column chromatography (SiO$_2$; CH$_2$Cl$_2$/ethyl acetate/MeOH 8:2:0.5): colourless wax, yield 14 mg (23%).

EXAMPLE 98
2,5-Dihydro-3,4-bis(N-trimethylsilylethoxymethylindol-2-yl)-1H-pyrrolo[sic]-2,5-dione 1.05 g (1.96 mmol) of 2-tributylstannyl-N-trimethylsilylethoxymethylindole in 5 ml of absol. DMF are added dropwise to a solution of 22.65 mg (0.02 mmol) of tetrakistriphenylphosphine palladium and 450.0 mg (1.77 mmol) of 3,4-dibromo-2,5-dihydro-1H-pyrrolo[sic]-2,5-dione in 10 ml of absol. DMF and the mixture is subsequently heated at 110° C. for 1 h. After cooling, it is poured onto 50 ml of H$_2$O and extracted with 2×50 ml of ether. The ether phases are washed with 100 ml of H$_2$O, dried over Na$_2$SO$_4$ and concentrated. The products can be separated by column chromatography (1. column: SiO$_2$; CH$_2$Cl$_2$/MeOH/hexane 20:1:2, 2. column: SiO$_2$; CH$_2$Cl$_2$/ethyl acetate 20:1). Yellow wax, yield 200 mg (19%).

The following were prepared analogously:

EXAMPLE 99
2,5-Dihydro-3,4-bisindol-2-yl-1H-pyrrolo [sic]-2,5-dione
M.p.: 197° C. (dec.) (CH$_2$Cl$_2$/hexane)

EXAMPLE 100
2,5-Dihydro-3,4-(N-phenylsulphonylindol-2-yl)-1H-pyrrolo [sic]-2,5-dione
M.p.: 196–197° C. (dec.) (acetone)

EXAMPLE 101
2,5-Dihydro-1-methyl-3,4-bis(N-phenylsulphonylindol-2-yl)-1H-pyrrolo[sic]-2,5-dione
M.p.: 147° C. (ether)

EXAMPLE 102
2,5-Dihydro-3,4-bisindol-2-yl-1-methyl-1H-pyrrolo[sic]-2,5-dione
M.p.: 247° C. (CH$_2$Cl$_2$/hexane) (dec.)

EXAMPLE 103
2,5-Dihydro-3-indol-2-yl-1-[2-(N,N-dimethylamino)-ethyl]-4-(N-phenylsulphonylindol-2-yl)-1H-pyrrolo[sic]-2,5-dione 2,5-Dihydro-1-[2-(N,N-dimethylamino)ethyl]-3,4-bis(N-phenylsulphonylindol-2-yl)-1H-pyrrolo[sic]-2,5-dione 4.12 mmol of 2,5-dihydro-3,4-bis(N-phenylsulphonylindol-2-yl)-1H-pyrrolo[sic]-2,5-dione are dissolved in 30 ml of absol. DMF, and 200 mg (5.00 mmol) of KH is [sic] cautiously added with stirring. After stirring for 1 h at room temp., the halide is added and the mixture is stirred at room temp. for 24 h. For work-up, the mixture is poured onto ice water. DMF and H$_2$O are distilled off in vacuo, the residue is dissolved in CH$_2$Cl$_2$ and the solution is washed with H$_2$O. After drying over Na$_2$SO$_4$, the solvent is stripped off in vacuo and the residue is purified by column chromatography (SiO$_2$; ethyl acetate). Yield 448 mg. 121 and 122 could be separated by column chromatography.

The following were obtained analogously:

EXAMPLE 104
2,5-Dihydro-3,4-bis(indol-2-yl)-1-[2-(N,N-dimethylamino)ethyl]-1H-pyrrolo[sic]-2,5-dione orange wax

EXAMPLE 105
1-(2-Bromoethyl)-2,5-dihydro-3,4-bis(N-phenylsulphonylindol-2-yl)-1H-pyrrolo[sic]-2,5-dione yellow-brown wax

EXAMPLE 106
1-(2-Bromoethyl)-2,5-dihydro-3-indol-2-yl-4-(N-phenylsulphonylindol-2-yl)-1H-pyrrolo[sic]-2,5-dione
M.p.: 160° C. (dec.)

EXAMPLE 107
1-(2-Bromoethyl)-2,5-dihydro-3,4-bis(indol-2-yl)-1H-pyrrolo[sic]-2,5-dione
M.p.: 104–109° C.

EXAMPLE 108
1-(2-Azidoethyl)-2,5-dihydro-3,4-bis(N-phenylsulphonyl-indol-2-yl)-1H-pyrrolo[sic]-2,5-dione
M.p.: 165° C. (dec.)

EXAMPLE 109
1-(2-Azidoethyl)-2,5-dihydro-3-indol-2-yl-4-(N-phenylsulphonylindol-2-yl)-1H-pyrrolo[sic]-2,5-dione
M.p.: 190° C. (dec.)

EXAMPLE 110
1-(2-Aminoethyl)-2,5-dihydro-3-indol-2-yl-4-(N-phenylsulphonylindol-2-yl)-1H-pyrrolo[sic]-2,5-dione
M.p.: 180° C. (dec.)

EXAMPLE 111
3-Bromo-4-(2-(3-(3-(4-bromo-1-methyl-2,5-dioxo-2,5-dihydro-1H-3-pyrrolyl)-1H-2-indolyl)propyl)-1H-3-indolyl)-1-methyl-2,5-dihydro-1H-pyrrolo[sic]-2,5-dione 200 mg (0.7 mmol) of 1,3-di(1H-indolyl)propane are dissolved in 4 ml of absol. THF and cooled to 0° C. 1.09 ml (1.7 mmol) of n-BuLi (1.6 M in hexane) are then added dropwise in the course of 30 min and the mixture is stirred at room temp. for 2 h. 0.46 g (1.71 mmol) of N-methyldibromomaleimide in 4 ml of absol. THF is then slowly added dropwise. The mixture is stirred overnight at room temp. and then poured onto 10 ml of 2 N HCl. The mixture is then extracted with ether (2×10 ml) and ethyl acetate (3×10 ml), the org. phase is dried over Na$_2$SO$_4$ and the solvent is stripped off in vacuo. The residue is purified by column chromatography (SiO$_2$, CH$_2$Cl$_2$). Red powder, yield: 0.20 g (44%).
M.p.: 160° C. (dec.)

The following were prepared analogously:

EXAMPLE 112
3-Bromo-4-(2-(5-(3-(4-bromo-1-methyl-2,5-dioxo-2,5-dihydro-1H-3-pyrrolyl)-1H-2-indolyl)pentyl)-1H-3-indolyl)-1-methyl-2,5-dihydro-1H-pyrrole-2,5-dione
M.p.: 137° C. (dec.)

EXAMPLE 113
3-Bromo-4-(2-(3-(3-(4-bromo-2,5-dioxo-2,5-dihydro-1H-3-pyrrolyl)-1H-2-indolyl)propyl)-1H-3-indolyl)-2,5-dihydro-1H-pyrrole-2,5-dione
M.p.: >350° C.

EXAMPLE 114
3-Bromo-4-(2-(5-(3-(4-bromo-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: >350° C. (dec.)

EXAMPLE 115
3-Bromo-4-(2-(8-(3-(4-bromo-2,5-dioxo-2,5-dihydro-1H-3-pyrrolyl)-1H-2-indolyl)octyl)-1H-3-indolyl)-2,5-dihydro-1H-pyrrole-2,5-dione
M.p.: 180° C. (dec.)

EXAMPLE 116
3-Bromo-4-(2-(2-(3-(4-bromo-1-methyl-2,5-dioxo-2,5-dihydro-1H-3-pyrrolyl)-1H-2-indolyl)ethyl)-1H-3-indolyl)-1-methyl-2,5-dihydro-1H-pyrrole-2,5-dione
M.p.: 179° C.

EXAMPLE 117
3-Bromo-4-(2-(4-(3-(4-bromo-1-methyl-2,5-dioxo-2,5-dihydro-1H-3-pyrrolyl)-1H-2-indolyl)butyl)-1H-3-indolyl)-1-methyl-2,5-dihydro-1H-pyrrole-2,5-dione
M.p.: 190° C. (dec.)

EXAMPLE 118
3-Bromo-4-(2-(8-(3-(4-bromo-1-methyl-2,5-dioxo-2,5-dihydro-1H-3-pyrrolyl)-1H-2-indolyl)octyl)-1H-3-indolyl)-1-methyl-2,5-dihydro-1H-pyrrole-2,5-dione
M.p.: 185° C. (dec.)

EXAMPLE 119
3-Bromo-4-(2-(10-(3-(4-bromo-1-methyl-2,5-dioxo-2,5-dioxo-2,5-dihydro-1H-3-pyrrolyl)-1H-2-indolyl)decyl)-1H-3-indolyl)-1-methyl-2,5-dihydro-1H-pyrrole-2,5-dione
M.p.: 164° C. (dec.)

EXAMPLE 120
3-Bromo-4-(2-(10-(3-(4-bromo-2,5-dioxo-2,5-dihydro-1H-3-pyrrolyl)-1H-2-indolyl)decyl)-1H-3-indolyl)-2,5-dihydro-1H-pyrrole-2,5-dione
M.p.: 164° C. (dec.)

EXAMPLE 121
3-Bromo-4-(2-(12-(3-(4-bromo-1-methyl-2,5-dioxo-2,5-dihydro-1H-3-pyrrolyl)-1H-2-indolyl)doceyl)-1H-3-indolyl)-1-methyl-2,5-dihydro-1H-pyrrole-2,5-dione
M.p.: 126–129° C.

The following was obtained by reaction of the compound of Example 114 with dimethylamine:

EXAMPLE 122
3-N,N-dimethylamino-4-(2-(5-(3-(4-N,N-dimethylamino-2,5-dioxo-2,5-dihydro-1H-3-pyrrolyl)-1H-2-indolyl)pentyl)-1H-3-indolyl)-2,5-dihydro-1H-pyrrole-2,5-dione

EXAMPLE 123
1-Methyl-3-(1-pyrrolidinyl)-4-(2-(5-(3-(1-methyl-4-(1-pyrrolidinyl)-2,5-dioxo-2,5-dihydro-1H-3-pyrrolyl)-1H-2-indolyl)pentyl)-1H-3-indolyl)-2,5-dihydro-1H-pyrrole-2,5-dione 1.0 g (1.5 mmol) of 3-bromo-4-(2-(5-(3-(4-bromo-1-methyl-2,5-dioxo-2,5-dihydro-1H-3-pyrrolyl)-1H-2-indolyl)pentyl)-1H-3-indolyl)-1-methyl-2,5-dihydro-1H-pyrrole-2,5-dione is dissolved in 5 ml (60.6 mmol) of pyrrolidine and stirred overnight at room temp. Excess pyrrolidine is then distilled off. The residue is completely freed from solvent residues in an oil-pump vacuum and then purified by column chromatography (SiO$_2$, CH$_2$Cl$_2$/ethyl acetate 95:5). Yield: 480 mg (49%).
M.p.: 289° C.

The following were prepared analogously:

EXAMPLE 124
1-Methyl-3-(1-piperidinyl)-4-(2-(5-(3-(1-methyl-4-(1-piperidinyl)-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 262° C.

EXAMPLE 125
1-Methyl-3-(1-morpholinyl)-4-(2-(5-(3-(1-methyl-4-(1-morpholinyl)-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 168–170° C.

EXAMPLE 126
1-Methyl-3-(1-tetrahydroisoquinolinyl)-4-(2-(5-(3-(1-methyl-4-(1-tetrahydroisoquinolinyl)-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 141–142° C.

EXAMPLE 128 [sic]
1-Methyl-3-(1-(4-(3-trifluoromethylphenyl)piperazinyl)-4-(2-(5-(3-(1-methyl-4-(1-(4-(3-trifluoromethylphenyl)piperazinyl))-2,5-dioxo-2,5-dihydro-1H-3-pyrrolyl-1H-2-indolyl)pentyl)-1H-3-indolyl)-2,5-dihydro-1H-pyrrole-2,5-dione
M.p.: 140–141° C.

EXAMPLE 128
1-Methyl-3-(1-(4-isopropylaminocarbonylmethyl-piperazinyl))-4-(2-(5-(3-(1-methyl-4-(1-(4-isopropylamino-carbonylmethylpiperazinyl))-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 126–128° C.

EXAMPLE 129
1-Methyl-3-(1-(4-isopropylaminocarbonylmethyl-piperazinyl)-4-(2-(5-(3-(4-bromo-1-methyl-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 156° C.

EXAMPLE 130
1-Methyl-3-(1-(4-pyrrolidinylcarbonylmethylpiperazinyl))-4-(2-(5-(3-(1-methyl-4-(1-(4-pyrrolidinylcarbonyl-methylpiperazinyl))-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 158° C. (dec.)

EXAMPLE 131
1-Methyl-3-(1-(4-pyrrolidinylcarbonylmethylpiperazinyl))-4-(2-(5-(3-(4-bromo-1-methyl-2,5-dioxo-2,5-dihydro-1H-3-pyrrolyl)-1H-2-indolyl)pentyl)-1H-3-indolyl)-2,5-dihydro-1H-pyrrole-2,5-dione
M.p.: 158–159° C.

EXAMPLE 132
1-Methyl-3-(1-(4-piperidinopiperidinyl))-4-(2-(5-(3-(1-methyl-4-(1-(4-piperidinopiperidinyl))-2,5-dioxo-2,5-dihydro-1H-3-pyrrolyl)-1H-2-indolyl)pentyl)-1H-3-indolyl)-2,5-dihydro-1H-pyrrole-2,5-dione M.p.: 230–232° C. (dec.)

EXAMPLE 133
1-Methyl-3-(1-(4-piperidinopiperidinyl))-4-(2-(5-(3-(4-bromo-1-methyl-2,5-dioxo-2,5-dihydro-1H-3-pyrrolyl)-1H-2-indolyl)pentyl)-1H-3-indolyl)-2,5-dihydro-1H-pyrrole-2,5-dione M.p.: 162–164° C.

EXAMPLE 134
1-Methyl-3-(1-(4-ethoxycarbonylpiperazin-1-yl))-4-(2-(5-(3-(1-methyl-(4-ethoxycarbonylpiperazin-1-yl)-2,5-dioxo-2,5-dihydro-1H-3-pyrrolyl)-1H-2-indolyl)pentyl)-1H-3-indolyl)-2,5-dihydro-1H-pyrrole-2,5-dione M.p.: 149–150° C.

EXAMPLE 135
1-Methyl-3-(1-(4-(N-(4-hydroxyphenyl)ethylamine))-4-(2-(5-(3-(1-methyl-(4-bromo-2,5-dioxo-2,5-dihydro-1H-3-pyrrolyl)-1H-2-indolyl)pentyl)-1H-3-indolyl)-2,5-dihydro-1H-pyrrole-2,5-dione M.p.: 120–122° C. (dec.)

EXAMPLE 136
1-Methyl-3-(1-(4-(N-1,2-diaminoethyl)-4-(2-(4-(3-(1-methyl-(4-bromo-2,5-dioxo-2,5-dihydro-1H-3-pyrrolyl)-1H-2-indolyl)pentyl)-1H-3-indolyl)-2,5-dihydro-1H-pyrrole-2,5-dione M.p.: 180° C. (dec.)

EXAMPLE 137
1-Methyl-3-(1-(4-(N-1,2-diaminoethyl)-4-(2-(4-(3-(1-methyl-(4-(N-1,2-diaminoethyl)-2,5-dioxo-2,5-dihydro-1H-3-pyrrolyl)-1H-2-indolyl)butyl)-1H-3-indolyl)-2,5-dihydro-1H-pyrrole-2,5-dione M.P.: >240° C. (dec.)

EXAMPLE 138
4,39-Dimethyl-1,4,14,29,39,42-hexaazaoctacyclo-[40.2.2.0(2,6).0(7,15).0(8,13).0(28,36).0(30,35).0(37,41)]hexatetraconta-2(6),7(15),8(13),9,11,28(36),30(35),31,33,37(41)-decaen-3,5,38,40-tetraone 0.75 mmol of 3-bromo-4-(2-(12-(3-(4-bromo-1-methyl-2,5-dioxo-2,5-dihydro-1H-3-pyrrolyl)-1H-2-indolyl)dodecyl)-1H-3-indolyl)-1-methyl-2,5-dihydro-1H-pyrrole-2,5-dione is dissolved in 200 ml of absol. DMF, treated with 0.5 ml of abs. NEt$_3$ and heated to 80° C. The solution of 0.75 mmol of piperazine in 100 ml of absol. DMF and 0.5 ml of NEt$_3$ is then slowly added dropwise to the warm solution and the mixture is then stirred at 80° C. for 48 h. The solvent is then removed in vacuo to the greatest possible extent and the residue is treated with 100 ml of 1N HCl. This solution is then extracted with ethyl acetate (in total about 600 ml), the combined extracts are dried over Na$_2$SO$_4$ and the solvent is stripped off in vacuo. Purification is carried out by column chromatography (SiO$_2$, CH$_2$Cl$_2$/EA9.5:0.5) orange crystals, yield: 0.267 g (52%).

M.p.: 194–195° C.

The following were prepared analogously:

EXAMPLE 139
8,43-Dimethyl-5,8,18,33,43,46-hexaazanonacyclo-[44.2.2.2(2,5).0(6,10).0(11,19).0(12,17).0(32,40).0(34,39).0(41,45)]dopentaconta-6(10),11(19), -12(17),13,15,32(40),34(39),35,37,41(45)-decaen-7,9,42,44-tetraone M.p.: >250° C.

EXAMPLE 140
9,44-Dimethyl-6,9,19,34,44,47-hexaazanonacyclo-[45.2.2.2(3,6).0(7,11).0(12,20).0(15,18).0(33, 412).0(35,40).0(42,46)]tripentaconta-7(11),12(20), -13(18),14,16,33(41),35(40),36,38,44(46)-decaen-8,10,43,45-tetraone M.p.: 286° C. (dec.)

EXAMPLE 141
10,45-Dimethyl-7,10,20,35,45,48-hexaazanonacyclo-[46.2.2.2(4,7).0(8,12).0(13,21).0(14,19).0(34, 42).0(36,41).0(43,47)]tetrapentaconta-8(12),13(21), -14(19),15,17,34(42),36(41),37,39,43(47)-decaen-9,11,44,46-tetraone M.p.: >250° C.

EXAMPLE 142
11,46-Dimethyl-8,11,21,36,46,49-hexaazanonacyclo-[47.2.2.2(5,8).0(9,13).0(14,22).0(15,20).0(35, 43).0(37,42).0(44,48)]pentapentaconta-9(13)[sic], -14(22),15(20),16,18,35(43),37(42),38,40,44(48)-decaen-10,12,45,47-tetraone M.p.: 276° C. (dec.)

EXAMPLE 143
13,48-Dimethyl-10,13,23,38,48,51-hexaazanonacyclo-[49.2.2.2(7,10).0(11,15).0(16,24).0(17,22).0(37,45). -0(39, 44).0(46,50)]heptapentaconta-11(15),16(24), -17(22),18,20,37(45),39(44),40,42,46(50)-decaen-12,14,47,49-tetraone M.p.: 245° C. (dec.)

EXAMPLE 144
14,49-Dimethyl-11,14,24,39,49,52-hexaazanonacyclo-[50.2.2.2(8,11).0(12,16).0(17,25).0(18,23).0(38,46). -0(40, 45).0(47,51)]octapentaconta-12(16),17(25),18(23), -19,21,38(46),40(45),41,43,47(51)-decaen-13,15,48,50-tetraone M.p.: 325° C. (dec.)

EXAMPLE 145
4,30-Dimethyl-1,4,14,20,30,33-hexaazaoctacyclo-[31.2.2.0(2,6).0(7,15).0(8,13).0(19,27).0(21,26). -0(28,32)]heptatriaconta-2(6)[sic],7(15),8(13),9,11,-19(27),21(26),22,24,28(32)-decaen-3,5,29,31-tetraone M.p.: 314–318° C.

EXAMPLE 146
8,34-Dimethyl-5,8,18,24,34,37-hexaazanonacyclo-[35.2.2.2(2,5).0(6,10).0(11,19).0(12,17).0(23,31). -0(25,30).0(32,36)]tritetraconta-6(10),11(19),12(17), -13,15,23(31),25(30),26,28,32(36)-decaen-7,9,33,35-tetraone M.p.: 197–200° C.

EXAMPLE 147
9,35-Dimethyl-6,9,19,25,35,38-hexaazanonacyclo-[36.2.2.2(3,6).0(7,11).0(12,20).0(13,18).0(24,32). -0(26,31).0(33,37)]tetratetraconta-7(11),12(20),13(18), -14,16,24(32),26(31),27,29,33(37)-decaen-8,10,34,36-tetraone M.p.: 337° C. (dec.)

EXAMPLE 148
10,36-Dimethyl-7,10,20,26,36,39-hexaazanonacyclo-[37.2.2.2(4,7).0(8,12).0(13,21).0(14,19).0(25,33). -0(27,32).0(34,38)]pentatetraconta-8(12),13(21),14(19), -15,17,25(33),27(32),28,30,34(38)-decaen-9,11,35,37-tetraone M.p.: 245° C. (dec.)

EXAMPLE 149
11,37-Dimethyl-8,11,21,27,37,40-hexaazanonacyclo-[38.2.2.2(5,8).0(9,13).0(14,22).0(15,20).0(26,34). -0(28,33)

.0(35,39)]hexatetraconta-9(13),14(22),15(20), -16,18,26(34),28(33),29,31,35(39)-decaen-10,12,36,38-tetraone M.p.: 325° C. (dec.)

EXAMPLE 150

13,39-Dimethyl-10,13,23,29,39,42-hexaazanonacyclo-[40.2.2.2(7,10).0(11,15).1(16,24).0(17,22).0(28,36). -0(30,35).0(37,41)]octatetraconta-11(15),16(24),17(22), -18,20,28(36),30(35),31,33,37(41)-decaen-12,14,38,40-tetraone M.p.: 245° C. (dec.)

EXAMPLE 151

14,40-Dimethyl-11,14,24,30,40,43-hexaazanonacyclo-[41.2.2.2(8,11).0(12,16).0(17,25).0(18,23).0(29,37). -0(31,36).0(38,42)]nonatetraconta-12(16),17(25),18(23), -19,21,29(37),31(36),32,34,38(42)-decaen-13,15,39,41-tetraone M.p.: 325° C. (dec.)

EXAMPLE 152

1,4,14,22,32,35-Hexaazaoctacyclo-[33.2.2.0(2,6).0(7,15).0(8,13).0(21,29).0(23,28). -0(30,34)]nonatriaconta-2(6),7(15),8(13),9,11,21(29), -23(28),24,26,30(34)-decaen-3,5,31,33-tetraone M.p.: 314–318° C.

EXAMPLE 153

5,8,18,26,36,39-Hexaazanonacyclo-[37.2.2.2(2,5).0(6,10).0(11,19).0(12,17).0(25,33). -0(27,32).0(34,38)]pentatetraconta-6(10),11(19),12(17), -13,15,25(33),27(32),28,30,34(38)-decaen-7,9,35,37-tetraone M.p.: 197–200° C.

EXAMPLE 154

9,37-Dimethyl-6,9,19,27,37,40-hexaazanonacyclo-[38.2.2.2(3,6).0(7,11).0(12,20).0(13,18).0(26,34). -0(28,33).0(35,39)]hexatetraconta-7(11),12(20),13(18), -14,16,26(34),28(33),29,31,35(39)-decaen-8,10,36,38-tetraone M.p.: >350° C.

EXAMPLE 155

7,10,20,28,38,41-Hexaazanonacyclo[39.2.2.2(4,7). -0(8,12).0(13,21).0(14,19).0(27,35).0(29,34).0(36,40)]-heptatetraconta-8(12),13(21),14(19),15,17,27(35), -29(34),30,32, 36(40)-decaen-9,11,37,39-tetraone M.p.: 290–292° C.

EXAMPLE 156

11,39-Dimethyl-9,11,21,29,39,42-hexaazanonacyclo-[40.2.2.2(5,8).0(9,13).0(14,22).0(15,20).0(28,36). -0(30,35).0(37,41)]octatetraconta-9(13),14(22),15(20), -16,18,28(36),30(35),31,33,37(41)-decaen-10,12,38,40-tetraone M.p.: 310° C. (dec.)

EXAMPLE 157

13,41-Dimethyl-10,13,23,31,41,44-hexaazanonacyclo-[42.2.2.2(7,10).0(11,15).0(16,24).0(17,22).0(30,38). -0(32,37).0(39,43)]pentaconta-11(15),16(24),17(22),18,-20,30(38),32(37),33,35,39(43)-decaen-12,14,40,42-tetraone M.p.: 310° C. (dec.)

EXAMPLE 158

14,42-Dimethyl-11,14,24,32,42,45-hexaazanonacyclo-[43.2.2.2(8,11).0(12,16).0(17,25).0(18,23).0(31,39). -0(33,38).0(40,44)]unpentaconta-12(16),17(25),18(23), -19,21,31(39),33(38),34,36,40(44)-decaen-13,15,41,43-tetraone M.p.: 321–324° C.

EXAMPLE 159

6,13-Dimethyl-5,6,7,8,9,10,11,12,13,14,19,20,21,22,23,-24-hexadecahydrodipyrrolo[3',4':15,16:3',4':5,6]indolo-[2',3':13,14][1,4]diazacyclohexadecyno[8,7:b]indol-5,-7,12,14-tetraone M.p.: >240° C.

EXAMPLE 160

1,4,14,29,39,42-Hexaazaoctacyclo[40.2.2.0(2,6). -0(7,15).0(8,13).0(28,36).0(30,35).0(37,41)]hexatetra-conta-2(6),7(15),8(13),9,11,28(36),30(35),31,33,37(41) -decaen-3,5,38,40-tetraone M.p.: 194–195° C.

EXAMPLE 161

5,8,18,33,43,46-Hexaazanonacyclo[44.2.2.2(2,5). -0(6,10).0(11,19).0(12,17).0(32,40).0(34,39). -0(41,45)]dopentaconta-6(10),11(19),12(17),13,15,-32(40),34(39),35,37,41 (45)-decaen-7,9,42,44-tetraone M.p.: 236–238° C.

EXAMPLE 162

6,9,19,34,44,47-Hexaazanonacyclo[45.2.2.2(3,6).0(7,11) -.0(12,20).0(15,18).0(33,412)[sic].0(35,40).0(42,46)]-tripentaconta-(11),12(20),13(18),14,16,33(41), -35(40),36,38,42 (46)-decaen-8,10,43,45-tetraone M.p.: 231–233° C.

EXAMPLE 163

7,10,20,35,45,48-Hexaazanonacyclo[46.2.2.2(4,7). -0(8,12).0(13,21).0(14,19).0(34,42).0(36,41).0(43,47)]-tetrapentaconta-8(12),13(21),14(19),15,17,34(42), -36(41),37,39,43(47)-decaen-9,11,44,46-tetraone M.p.: 209–211° C.

EXAMPLE 164

8,11,21,36,46,49-Hexaazanonacyclo[47.2.2.2(5,8). -0(9,13).0(14,22).0(15,20).0(35,43).0(37,42).0(44,48)]-pentapentaconta-9(13),14(22),15(20),16,18,35(43), -37(42),38, 40,44(48)-decaen-10,12,45,47-tetraone M.p.: 282–284° C.

EXAMPLE 165

10,13,23,38,48,51-Hexaazanonacyclo[49.2.2.2(7,10). -0(11,15).0(16,24).0(17,22).0(37,45).0(39,44).0(46,50)]-heptapentaconta-11(15),16(24),17(22),18,20,37(45),39(44),40,42,46(50)-decaen-12,14,47,49-tetraone M.p.: 176–179° C.

EXAMPLE 166

11,14,24,39,49,52-Hexaazanonacyclo[50.2.2.2(8,11). -0(12,16).0(17,25).0(18,23).0(38,46).0(40,45).0(47,51)]-octapentaconta-12(16),17(25),18(23),19,21,38(46), -40(45),41,43,47(51)-decaen-13,15,48,50-tetraone M.p.: 147–150° C.

EXAMPLE 167

1,4,14,20,30,33-Hexaazaoctacyclo[31.2.2.2(2,6). -0(7,15).0(8,13).0(19,27).0(21,26).0(28,32)]-heptatriaconta-2(6),7(15),8(13),9,11,19(27), -21(26),22,24,28(32)-decaen-3,5,29,31-tetraone M.p.: 350° C. (dec.)

EXAMPLE 168

5,8,18,24,34,37-Hexaazanonacyclo[35.2.2.2(2,5). -0(6,10).0(11,19).0(12,17).0(23,31).0(25,30).0(32,36)]-tritetraconta-6(10),11(19),12(17),13,15,23(31), -25(30),26,28,32(36)-decaen-7,9,33,35-tetraone M.p.: 285° C. (dec.)

EXAMPLE 169

6,9,19,25,35,38-Hexaazanonacyclo[36.2.2.2(3,6). -0(7,11).0(12,20).0(13,18).0(24,32).0(26,31).0(33,37)]- tetratetraconta-7(11),12(20),13(18),14,16,24(32), -26(31), 27,29,33 (37)-decaen-8,10,34,36-tetraone
M.p.: 215° C.

EXAMPLE 170
7,10,20,26,36,39-Hexaazanonacyclo[37.2.2.2(4,7). -0(8,12) .0(13,21).0(14,19).0(25,33).0(27,32).0(34,38)]-pentatetraconta-8(12),13(21),14(19),15,17,25(33), -27(32), 28, 30,34(38)-decaen-9,11,35,37-tetraone
M.p.: 330° C. (dec.)

EXAMPLE 171
8,11,21,27,37,40-Hexaazanonacyclo[38.2.2.2(5,8). -0(9,13) .0(14,22).0(15,20).0(26,34).0(28,33).0(35,39)]-hexatetraconta-9(13),14(22),15(20),16,18,26(34), -28(33), 29, 31,35(39)-decaen-10,12,36,38-tetraone
M.p.: 335.5° C. (dec.)

EXAMPLE 172
10, 13,23,29,39,42-Hexaazanonacyclo[40.2.2.2(7,10). -0(11,15).0(16,24).0(17,22).0(28,36).0(30,35).0(37,41)]-octatetraconta-11(15),16(24),17(22),18,20,28(36), 30(35), 31,33,37(41)-decaen-12,14,38,40-tetraone
M.p.: 243–245° C.

EXAMPLE 173
11,14,24,30,40,43-Hexaazanonacyclo[41.2.2.2(8,11). -0(12, 16).0(17,25).0(18,23).0(29,37).0(31,36).0(38,42)]-nonatetraconta-12(16),17(25),18(23),19,21,29(37), -31(36), 32,34,38(42)-decaen-13,15,39,41-tetraone
M.p.: 258–260° C.

EXAMPLE 174
4,32-Dimethyl-1,4,14,22,32,35-hexaazaoctacyclo-[33.2.2.2 (2,6).0(7,15).0(8,13).0(21,29).0(23,28). -25 0(30,34)] nonatria conta-2(6)[sic],7(15),8(13),9,11,-21(29),23(28),24, 26,30(34)-decaen-3,5,31,33-tetraone
M.p.: >350° C.

EXAMPLE 175
8,36-Dimethyl-5,8,18,26,36,39-hexaazanonacyclo-[37.2.2.2(2,5).0(6,10).0(11,19).0(12,17). -0(25,33).0(27,32) .0(34.38)]pentatetraconta-6(10),11(19),12(17),13,15,25 (33),27(32),28,30,34(38)-decaen-7,9,35,37-tetraone
M.p.: 310° C. (dec.)

EXAMPLE 176
10,38-Dimethyl-7,10,20,28,38,41-hexaazanonacyclo-[39.2.2.2(4,7).0(8,12).0(13,21).0(14,19). -0(27,35).0(29,34) .0(36.40)]heptatetraconta-8(12),13(21),14(19),15,17,27 (35),29(34),30,32,36(40)-decaen-9,11,37,39-tetraone
M.p.: 280° C. (dec.)

EXAMPLE 177
13,46-Dimethyl-1,7,10,13,23,36,46,49-octaazanonacyclo-[47.2.2.2(7,10).0(11,15).0(16,24).0(17,22). -0(35,43).0(37, 42).0(44,48)]pentapentaconta-11(15),16(24),17(22),18,20, 35(43),37(42), 38,40,44(48)-decaen-12,14,45,47-tetraone
M.p.: >220° C.

EXAMPLE 178
4,31-Dimethyl-1,4,14,21,31,34-hexaazaoctacyclo-[32.2.2.2 (2,6).0(7,15).0(8,13).0(20,28). -0(22,27).0(29,33)]octtriac onta-2(6) [sic],7(15), -8(13),9,11,20(28),22(27),23,25,29 (33)-decaen-3,5,309[sic],32-tetraone
M.p.:>240° C. (dec.)

EXAMPLE 179
8,35-Dimethyl-5,8,18,25,35,38-hexaazanonacyclo-[36.2.2.2(2,5).0(6,10).0(11,19).0(12,17). -0(24,32).0(26,31) .0(33,37)]tetratetraconta-6(10),11(19),12(17),13,15,24(32), 26(31),27,29,33(37)-decaen-7,9,34,36-tetraone, m.p.:>240 (dec.)

EXAMPLE 180
(1-(2-Dimethylaminoethyl)-1H-3-indolyl)(1H-3-indolyl)-1-methanone 0.5 g of bis(indol-3-yl)methanone is dissolved in 30 ml of acetone. After addition of 0.92 g of $K_2CO_3$ and 0.27 g of 2-dimethylamino-1-chloroethane hydrochloride, the mixture is heated to reflux for 70 h. The acetone is stripped off and the residue is treated with 30 ml of water and 30 ml of ethyl acetate. After stirring for 15 min, the org. phase is separated off and the aqueous phase is extracted by shaking a further two times with 15 ml of ethyl acetate each time. The combined org. phases are dried over $Na_2SO_4$ and the solvent is stripped off. Purification is carried out by column chromatography (SiO2, EA/MeOH 10:1). Yield: 0.14 g (20%)

M.p.: 180–182° C.

The following were prepared analogously:

EXAMPLE 181
(1-(2-Morpholinoethyl)-1H-3-indolyl)(1H-3-indolyl)-1-methanone
M.p.: 192–194° C.

EXAMPLE 182
Bis(1-(2-morpholinoethyl)-1H-3-indolyl)-1-methanone
M.p.: 91–93° C.

EXAMPLE 183
(1-(2-Piperidinoethyl)-1H-3-indolyl)(1H-3-indolyl)-1-methanone
M.p.: 223–225° C.

EXAMPLE 184
Bis(1-(2-piperidinoethyl)-1H-3-indolyl)-1-methanone
M.p.: 152–155° C.

EXAMPLE 185
(1-(3-Dimethylaminopropyl)-1H-3-indolyl)(1H-3-indolyl)-1-methanone
M.p.: 144–146° C.

EXAMPLE 186
(1-(3-Pyrrolidinopropyl)-1H-3-indolyl)(1H-3-indolyl)-1-methanone
M.p.: 148–152° C.

EXAMPLE 187
(1-(2-Dimethylaminoethyl)-1H-2-indolyl)(1H-2-indolyl)-1-methanone
M.p.: 147–150° C.

EXAMPLE 188
(1-(2-Morpholinoethyl)-1H-2-indolyl)(1H-2-indolyl)-1-methanone
Wax

EXAMPLE 189
(1-(2-Piperidinoethyl)-1H-2-indolyl)(1H-2-indolyl)-1-methanone
Wax

EXAMPLE 190
(1-(2-Pyrrolidinoethyl)-1H-2-indolyl)(1H-2-indolyl)-1-methanone
Wax

EXAMPLE 191
11,46-Dimethyl-21,36-bis(2-(1-piperidinyl)ethyl-8,11,21, 36,46,49-hexaazanonacyclo-[47.2.2.2(5,8). -0(9,13).0(14, 22).0(15,20).0(35,43).0(37,42). -0(44,48(pentapentaconta-9 (13),14(22),15(20), -16,18,35,(43),37(42),38,40,44(48)-decaen-10,12,45,47-tetraone M.p.: 125–130° C.

EXAMPLE 192
3,3-Dimethoxydiglyoxyl-1,8-(2,2'-bisindolyl)octane

Oxalyl dichloride is added dropwise under an $N_2$ atmosphere to a solution of 1.15 g (4.00 mmol) of 1,8-(2,2'-bisindolyl)octane in 20 ml of absol. THF at 0° C. and the mixture is stirred at room temperature for 2 h. 20 ml of MeOH are then allowed to run in dropwise. The mixture is stirred overnight at room temperature. For work-up, the mixture is treated with 100 ml of 1 N HCl, neutralized with 2 N NaOH and the mixture is extracted with EA (3×25 ml). After drying over $NaSO_4$ [sic], the solvent is stripped off.

M.p.: >250° C. (dec.)

EXAMPLE 193
3-(2-(4-(1H-2-Indolyl)butyl)-1H-3-indolyl)-1-methyl-2,5-pyrrolidinedione A solution of 240 mg (0.50 mmol) of 3-bromo-4-(2-(4-(1H-2-indolyl)butyl)-1H-3-indolyl)-1-methyl-2,5-dihydro-1H-pyrrole-2,5-dione and 140 mg (0.25 mmol) of Pd(OH)$_2$/C (20%) in 30 ml of MeOH is stirred under an $H_2$ atmosphere at room temperature for 24 h. For work-up, the mixture is filtered, the filtrate is concentrated and the residue is purified by column chromatography ($SiO_2$:$CH_2Cl_2$/EA 95:5). On concentrating the pure fraction, the product is crystallized by addition of PE. Yield: 48.0 mg (24%), beige powder M.p.: 180–182° C.

EXAMPLE 194
Test for Measurement of the Inhibition of PDGF-dependent Tyrosine Phosphorylation for Compounds According to the Invention Swiss 3T3 cells are cultured for 1 week under standard conditions (DMEM with glutamine, 4 g of glucose/l, 10% FCS, antibiotics, 5–7.5% $CO_2$) and are confluent and no longer proliferating at the end of the culture period. The medium is replaced by serum-free DMEM and the cells are incubated at 37° C. for 2 h with the compounds according to the invention or, in control experiments, with DMSO (final concentration 0.1–1%). The cells are then stimulated at room temperature for 5 min by addition of PDGF-BB to a final concentration of 100 ng/ml, in controls addition of the corresponding solvent takes place. The cells are then washed twice with ice-cold PBS and lysed in a Triton X-100-containing lysis buffer (composition and process as described in Selective platelet-derived growth factor receptor kinase blockers reverse sis-transformation M. Kovalenko, A. Gazit, A. Böhmer, C. Rorsman, L. R önnstrand, C. H. Heldin, J. Waltenberger, F. D. Böhmer, A. Levitzki (1994) Cancer Res. 54, 6106–6114). The lysates are centrifuged and the protein concentration is determined. 10 μg of lysate protein are applied directly to nitrocellulose membranes (Dot-blot apparatus or corresponding multi-well plates with nitrocellulose bases).

Tyrosine phosphorylation is detected by standard processes using antiphosphophotyrosine [sic] antibodies. Typically, a monoclonal antiphosphotyrosine antibody, conjugated to horseradish peroxidase (POD), and detection of the POD activity by means of chemiluminescence detection is used. Quantification is carried out either by grey value analyses of films used for the luminescence detection or directly using a luminometer. Customarily, the PDGF stimulation of the cells results in a 3- to 10-fold increase in the signal.

The compounds were primarily employed in duplicate in the final concentration 10 μg/ml. In the case of active compounds, a titration was carried out in the stages 30 μM, 10 μM, 3 μM, 1 μM, 0.3 μM and 0.1 μM as a duplicate determination. The results are shown in Table 1.

TABLE 1

| Example | Compound | IC 50 (μM) |
|---------|----------|------------|
| 19 | Bisindol-2-ylmethan-1-one | 1 |
| 20 | (5-Methoxyindol-2-yl)-(indol-2-yl)methan-1-one | 0.1–0.3 |
| 21 | Bis(5-methoxyindol-2-yl)-1-methanone | 10–30 |
| 28 | Benzo[b]thiophen-2-yl (5-methoxy-1H-2-indolyl)-1-methanone | 1 |
| 43 | 5-Hydroxy-1H-2-indolyl(1H-2-indolyl) methanone | 0.1–0.3 |
| 45 | 1H-2-Indolyl[5-(2-morpholin-1-ylethyloxy)-1H-2-indolyl]methanone | 1–3 |
| 48 | 1H-2-Indolyl[5-(2-dimethylamino-ethyloxy)-1H-2-indolyl]methanone | 0.3–1 |
| 53 | [2-(1H-2-Indolylcarbonyl)-1H-5-indolyl)] ethanoate | 0.1–0.3 |
| 55 | [2-(1H-2-Indolylcarbonyl)-1H-5-indolyl)] butanoate | 1–3 |
| 56 | [2-(1H-2-Indolylcarbonyl)-1H-5-indolyl)] 2-(N,N)-dimethylaminoethanoate | 0.1 |
| 57 | [2-(1H-2-Indolylcarbonyl)-1H-5-indolyl)] propanoate | 0.3–1 |
| 58 | [2-(1H-2-Indolylcarbonyl)-1H-5-indolyl)] 2-thiophenylethanoate | 0.3–1 |

The qualitative detection of the effects on the tyrosine phosphorylation of the PDGF receptor and cellular substrate is carried out by analysis of the cell lysates by means of polyacrylamide gel electrophoresis and immunoblotting using anti-phosphotyrosine antibodies according to standard processes.

The compounds according to the invention were furthermore investigated in vitro using isolated plasma membranes of Swiss 3T3 cells and using PDGF receptor purified from overexpressing cells, tested in intact A431 cells (and in some cases also in Swiss 3T3 plasma membranes) for possible inhibition of the EGF receptor tyrosine kinase and tested for inhibition of recombinant Src kinase. The results are chosen in Table 2.

DNA synthesis tests in Swiss 3T3 cells which are stimulated with different growth factors are suitable for characterizing selective antiproliferative actions of receptor tyrosine kinase inhibitors. The compounds were investigated with respect to their action on the DNA sythesis stimulated in these cells by PDGF-BB, bFGF, FCS and the combination of EGF and insulin. These stimulants are approximately equipotent and increase the DNA synthesis in previously growth-arrested Swiss 3T3 cells to 5- to 20-fold. The dose dependencies of the corresponding experiments and the IC50 values obtained are likewise shown in Table 2.

Furthermore, the compounds were investigated for a possible antitransforming action using sis-transformed NIH3T3 cells. In these cells, a transformed phenotype characterized, inter alia, by irregular multilayered growth and colony formation in soft agar is maintained by expression of PDGF-BB and permanent activation of the endogenous PDGF receptors. The IC50 values obtained are likewise shown in Table 2.

Accordingly, actions on the PDGF receptor kinase by the compounds were found in the following tests:

PDGF receptor autophosphorylation in intact Swiss 3T3 cells

PDGF receptor autophosphorylation in isolated membranes of Swiss 3T3 fibroblasts PDGF receptor autophosphorylation in purified receptor preparations No actions were observed in analogous tests with the receptor tyrosine kinase for the epidermal growth factor and with the cytosolic tyrosine kinase Src up to a concentration of of [sic] 30 M. The compounds thus have specificity for the inhibition of the PDGF receptor tyrosine kinase in relation to other tyrosine kinases.

TABLE 2

| Test | IC 50 ($\mu$M) | | |
|---|---|---|---|
| | Example 19 | Example 20 | Example 21 |
| PDGFR phosphorylation in vivo (Swiss 3T3 cells) | 1 | 0.1–0.3 | 10–30 |
| PDGFR phosphorylation in vitro (Swiss 3T3 membranes) | 0.3–1 | <0.03 | n.d. |
| PDGFR phosphorylation in vitro (purified PDGF receptor) | 0.1–0.3 | n.d. | n.d. |
| EGFR phosphorylation in vivo (A 431 cells) | >10 | >10 | n.d. |
| src kinase phosphorylation in vivo (src NIH cells) | >30 | >30 | n.d. |
| Reversion of the transformed morphology of sis-3T3 cells | +++ | n.d. | n.d. |
| DNA synthesis (Swiss 3T3 cells) | | | |
| PDGF-stimulated | 3–10 | n.d | n.d |
| FGG-stimulated | 3–10 | n.d. | n.d. |
| EGF/insulin-stimulated | >30 | n.d. | n.d. |
| 10% FCS | >30 | n.d. | n.d. |
| Colony formation (sis-3T3 cells) | 3–10 | n.d | n.d |

What is claimed is:

1. Compounds having the formula XI

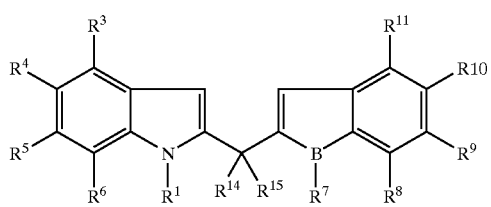

(XI)

wherein B is a nitrogen, oxygen or sulphur atom;

$R^1$ and $R^7$ are identical or different and are hydrogen atoms, alkyl or aminoalkyl radicals, phenylsulphonyl radicals, alkylsilylmethoxymethyl radicals, a sugar or substituted sugar;

$R^4$ and $R^{10}$ are identical or different and in each case is a hydrogen atom, an alkoxy-, amino-, halogen-, cycloalkyl-, cycloheteroalkyl-, aryl-substituted alkyl, alkoxy or alkoxymethyl group, nitro group, or an O-alkoxy group of the formula —O—(C=O)—$R^{21}$, where $R^{21}$ is an alkoxy-, amino-, halogen-, cycloalkyl-, cycloheteroalkyl-, aryl- or heteroaryl-substituted alkyl, alkoxy or alkoxymethyl group;

$R^{14}$ and $R^{15}$ either together form an oxygen atom or $R^{14}$ is a hydroxyl group and $R^{15}$ is a hydrogen atom or $R^{14}$ and $R^{15}$ are hydrogen atoms; and $R^3$, $R^5$, $R^6$, $R^8$, $R^9$ and $R^{11}$ are identical or different and in each case is a hydrogen atom, an alkoxy-, amino-, halogen-, cycloalkyl-, cycloheteroalkyl-, aryl- or heteroaryl-substituted alkyl, alkoxy or alkoxymethyl group, nitro group, or an O-alkoxy group of the formula —O—(C=O)—$R^{21}$, where $R^{21}$ is an alkoxy-, amino-, halogen-, cycloalkyl-, cycloheteroalkyl-, aryl- or heteroaryl-substituted alkyl, alkoxy or alkoxymethyl group.

2. Bisindol-2-ylmethan-1-one according to claim 1.

3. (5-metoxyindol-2-yl)-(indol-2-yl)methan-1-one according to claim 1.

4. Bis(5-methoxyindol-2-yl)-1-methanone according to claim 1.

5. Benzo[b]thiophene-2-yl-(5-methoxy-1H-2-indolyl)-1-methanone according to claim 1.

6. 1H-2-Indolyl[5-(2-morpholin-1-ylethyloxy)-1H-2-indolyl] methanone according to claim 1.

7. Medicaments comprising a compound according to any one of claims 1, 2, 4, 5 or 6.

8. A method of inhibiting tyrosine kinase comprising administering an effective amount of the compound according to any one of claims 1, 2, 4, 5 or 6.

9. A method of inhibiting a Platelet-Derived Growth Factor (PDGF) receptor tyrosine kinase or a structurally related tyrosine kinase comprising administering an effective amount of the compound according to any one of claims 1, 2, 4, 5 or 6.

10. A method of treating tumors selected from the group consisting of gliomas, glioblastomas, sarcomas, mastocarcinomas, ovarian carcinomas and colonic carcinomas, comprising administering an effective amount of the compound according to any one of the claims 1, 2, 4, 5 or 6.

11. A method of treating arteriosclerosis, restenosis after balloon angioplasty, arthritis, or a fibriotic disease comprising administering an effective amount of the compound according to any one of claims 1, 2, 4, 5 or 6.

* * * * *